US00PP09499P

United States Patent [19]

Ebihara

[11] Patent Number: Plant 9,499

[45] Date of Patent: Apr. 9, 1996

[54] HYDRANGEA PLANT NAMED 'FRAU KATSUKO'

[75] Inventor: Hiroshi Ebihara, Ninomiya, Japan

[73] Assignee: Miyoshi & Co. Ltd., Tokyo, Japan

[21] Appl. No.: 412,520

[22] Filed: Mar. 29, 1995

[51] Int. Cl.[6] ..... A01H 5/00

[52] U.S. Cl. ..... Plt./67.1

[58] Field of Search ..... Plt./67.1

*Primary Examiner*—James R. Feyrer
*Attorney, Agent, or Firm*—James R. Cypher

[57] ABSTRACT

This invention relates to a new and distinct cultivar of *Hydrangea macrophylla* (Thunb.) named 'Frau Katsuko' which originated as a seedling from the inventor's controlled hybridization of the *Hydrangea macrophylla* cultivars 'Madam Blumkock' and 'Silver-Edge' and is distinguished from its parents by the combination of its pigmentation pattern in its sepals which is predominently colored with deep, irregular, white edges; its deeply serrated, ruffled edges; and its dense inflorescence that does not require staking for support. Pigmentation is darkest at base of sepal, fading slightly as it progresses along the length and width of the sepal, and then turns white as far as 5 mm from edge. The sepals of 'Madam Blumkock' are uniformy pigmented one color, while the sepals of 'Silver-Edge' are also uniformly pigmented except the sepal edges are white. The new variety 'Frau Katsuko' further possesses the favorable characteristics of a compact growth habit, long lasting large flowers and it is easily forced in a greenhouse for flowering in the spring without growth regulation.

1 Drawing Sheet

BACKGROUND OF THE INVENTION

This invention relates to a new and distinct cultivar of the Saxifragaceae family. The botanical name of the plant is *Hydrangea macrophylla* (Thunb.). The varietal denomination is 'Frau Katsuko'. The new cultivar originated as a seedling from the inventor's controlled crossing as pollen and seed parents, respectively, the varieties known as, 'Madam Blumkock' and 'Silver-Edge' in Tochigi-Prefecture, Japan. 'Frau Katsuko' was discovered and selected as one flowering plant within the progeny of the stated parentage in a controlled environment. 'Frau Katsuko' is distinguished from its parents, and all other varieties of *Hydrangea macrophylla* of which I am aware, by the combination of the attractive pigmentation pattern of its sepals which is predominently colored with deep, irregular, white edges; its deeply serrated, ruffled edges; and its dense inflorescence on a strong stem that does not require staking for support. This new cultivar has been successfully asexually reproduced under controlled environmental conditions at a nursery in Half Moon Bay, Calif. under the direction of the inventor over a three year period with its distinguishing characteristics remaining stable.

Sepal color of 'Frau Katsuko' is predominately blue or red with a deep irregular, white edge pattern, The pigmentation is darkest at the apex and fades slightly as it progresses across the length and width of the sepals, and then turns white as far as 5 mm from edge. Color pigmentation often reaches the edge of the sepal, but only at the apex. Sepal pigmentation of individual *Hydrangea macrophylla* plants depends on the nutrients and pH of the growing medium. The sepal coloration of the pollen parent 'Madam Blumkock',is uniformly pink. The sepals of seed parent, 'Silver-Edge', has a uniform red pigmentation with white edges. The new variety of Hydrangea as described herein is further characterized by its compact growth habit, the ease with which it can be forced in a greenhouse, and its large, long lasting flowers that do not need to be staked. Mature flowers slowly fade to green and ultimately brown with age.

Asexual reproduction was first accomplished when vegetative cuttings were taken by the inventor from the initially selected plant. Examination of asexually reproduced, successive generations grown in a controlled environment at Half Moon Bay, Calif. show that the combination of characteristics as herein disclosed for 'Frau Katsuko' is firmly fixed. Asexual reproduction of successive generations at Half Moon Bay was achieved by taking vegetative cuttings from selected plants over three years. Each new generation over the three years retained the combination of characteristics as herein disclosed for 'Frau Katsuko'.

DESCRIPTION OF THE DRAWINGS

The accompanying drawings consist of color photographs that show the typical plant form, including the inflorescence, foliage, and unique sepal pigmentation pattern. These color phtographic drawings show the red form of the new cultivar. The colors are represented as truly as possible using conventional photographic procedures. 'Frau Katsuko' is shown with a red and white sepal pigmentation pattern, but a blue and white pigmentation pattern is also possible by manipulation of the nutrient amendments and the pH of the growing medium.

THE PLANT

Figure 1:
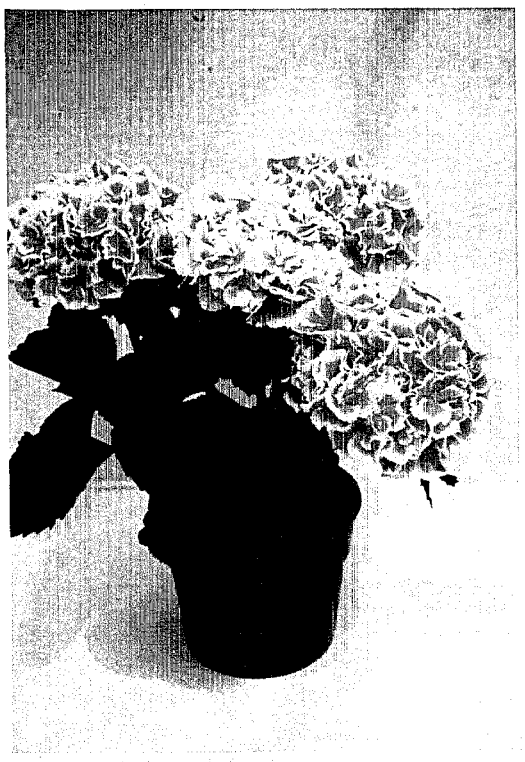
FIG. 1 is a view of the entire plant showing its form, compact growth habit, dark green foliage, inflorescence, and unique pigmentation pattern.
Figure 3:
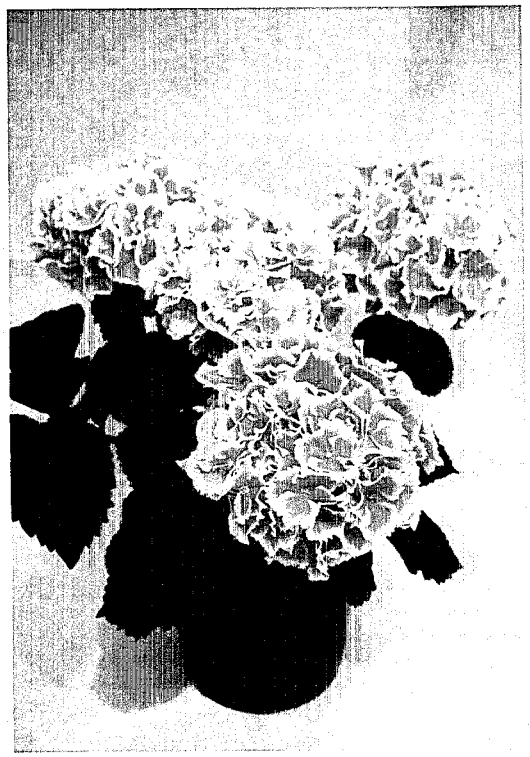
FIG. 3 is a close-up view of the flower heads of the new cultivar illustrating the unusual density of the large inflorescences. cl DESCRIPTION OF THE NEW PLANT 'Frau Katsuko' has not been observed under all possible environmental conditions. The phenotype may vary significantly with variations in environment such as temperature, light intensity and day length. The following is a detailed description of the new cultivar as forced under the prevailing daylengths at Half Moon Bay, Calif. during the winter months under commercial greenhouse conditions, as would be appropriate for the sale of the cultivar in the spring. The color determinations were made with The Royal Horticultural Society (R.H.S.) Colour Chart.
Figure 2:
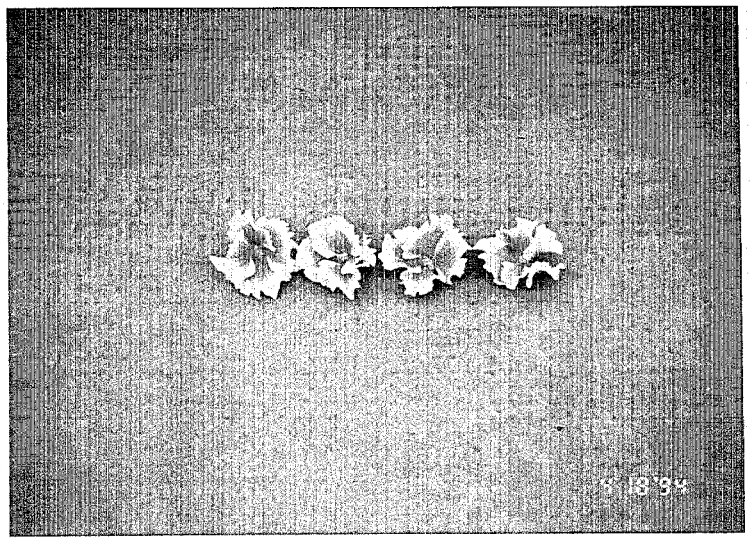
FIG. 2 is a close-up view of the individual florets illustrating the deep, irregular white edge; very serrated and ruffled edges and color pigmentation pattern.

Origin: Seedling.
Parentage:

*Seed parent.*—*Hydrangea macrophylla* DC var. *hortensia 'Silver-Edge'*.

*Pollen parent.*—*Hydrangea macrophylla* DC var. *hortensia 'Madam Blumkock'*.

Classification:

*Botanic.*—*Hydrangea macrophylla* (Thunb.) 'Frau Katsuko'.

*Commercial.*—Florist Hydrangea 'Frau Katsuko'.

Form: Upright, compact shrub.

Height: Flowering shoots range from 25 to 30 cm.

Growth: Upright, vigorous growth habit; forced without growth regulation and does not require staking to support the inflorescence.

Stems: Colorless lenticels; lateral buds are green with a reddish tip; reddish coloration above and below leaf attachment sites.

Branching: Excellent.

Foliage: Abundant.

*Size of leaf.*—As large as 135 mm long by 85 mm wide.

*Shape of leaf.*—Elliptic with acute base and apex; margins are serrate.

*Texture.*—Glabrous; veins dominate on the underside of the leaf and are sunken on the leaf surface.

*Color.*—Upper side is R.H.S. 137 A (green group); upper side covered by flower is R.H.S. 147 A (yellow-green group); under side is R.H.S. 137 C (green group); veins are R.H.S. 145 D (yellow-green group).

*Petioles.*—As long as 2.5 cm.

THE BUD

Form: Globose; with 4 to 5 connate petals. Center buds are non-sepalous. Marginal buds have sepals.

Size: 3 mm.

Aspect: Smooth.

Rate of opening: Buds with sepals opening more slowly than buds without sepals.

Sepals: Imbricated; deeply serrated and very ruffled. Early pigmentation ranges from R.H.S. 145 B to 150 D (yellow-green group).

Arrangement: Borne on 3, 4 or 5 branched panicles.

INFLORESCENCE

Time of blooming: Forced in 70 to 80 days at 15.5° C. night temperature.

Form: Paniculate. 100 or more individual flowers (florets) per inflorescence. Both sterile, sepalous florets and fertile, non-sepalous florets borne on the same penicle.

Size of inflorescence: Individual inflorescence size is dependent on the number of inflorescences. Large inflorescences have been measured with a 18 cm. diameter on a multi-flowered plant.

Shape: Spherical clusters of numerous small florets; sepalous florets are curved and the sepals of a floret overlap one another. Sepals elongate and become colored as the inflorescence matures.

Appearance: Showy.

Persistence: 4 plus weeks.

Fragrance: Faintly sweet when in full bloom.

Fruit: None.

Reproductive organs:

*Stamens.*—7 to 9 stamens. Pollen is white.

*Stigma.*—1 three-pronged stigma.

Sepalous florets:

*Number of sepals.*—4 or 5 sepals per floret, usually 4.

*Aspect of sepals.*—Smooth.

*Shape of sepals.*—Reniform with acuminate apex. Edges deeply serrated and very ruffled.

*Size of sepals.*—Usually 1 dominant sepal, 2 smaller but equally-sized sepals, and 1 small sepal. Large sepals can measure as much as 35 mm wide by 32 mm long.

*Coloration of sepals.*—Predominately red or blue with a deep irregular white edge. Pigmentation is darkest at base of sepal, fading slightly as it progresses along the length and width of the sepal, and then turns white as far as 5 mm from edge. Color pigmentation often reaches the edge of the sepal, but only at the apex. As inflorescences age the coloration of entire sepal fades to cream, then green, and then brown. Sepal color is not detailed using the R.H.S. Colour Chart as the sepal color is determined by the soil pH and nutritional amendments supplied.

I claim:

1. A new and distinct hybrid plant variety of the Saxifragaceae family substantially as herein shown and described.

* * * * *